(12) United States Patent
Larsen et al.

(10) Patent No.: US 10,258,472 B2
(45) Date of Patent: Apr. 16, 2019

(54) BONE GRAFT CAGE

(71) Applicant: DePuy Synthes Products, Inc., Raynham, MA (US)

(72) Inventors: Scott Larsen, West Chester, PA (US); Ross Hamel, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/675,266

(22) Filed: Mar. 31, 2015

(65) Prior Publication Data

US 2016/0287390 A1    Oct. 6, 2016

(51) Int. Cl.
  *A61F 2/28* (2006.01)
  *A61L 31/06* (2006.01)
  *A61F 2/30* (2006.01)

(52) U.S. Cl.
  CPC ............ *A61F 2/2846* (2013.01); *A61L 31/06* (2013.01); *A61F 2002/2825* (2013.01); *A61F 2002/2853* (2013.01); *A61F 2002/3024* (2013.01); *A61F 2002/30293* (2013.01); *A61L 2430/02* (2013.01)

(58) Field of Classification Search
  CPC ............ A61F 2/2846; A61F 2230/0091; A61F 2002/30291; A61F 2002/30293
  See application file for complete search history.

(56) References Cited

U.S. PATENT DOCUMENTS 3,710,789 A * 1/1973 Ersek ............... A61B 17/8085
                                                    606/281
5,676,697 A * 10/1997 McDonald ............ A61F 2/90
                                                    623/1.35
5,676,699 A * 10/1997 Gogolewski .......... A61F 2/2846
                                                    623/16.11
(Continued)

FOREIGN PATENT DOCUMENTS

CN       103298429       9/2013
EP       0551611         7/1993
(Continued)

OTHER PUBLICATIONS

Gugala et al., "New Approaches in the Treatment of Critical-Size Segmental Defects in Long Bones", Macromol. Symp., No. 253, WILEY-VCH Verlag GmbH & Co. KGaA, Weinheim, 2007, pp. 147-161.

*Primary Examiner* — Bruce E Snow
*Assistant Examiner* — Melissa Hoban
(74) *Attorney, Agent, or Firm* — Fay Kaplun & Marcin, LLP (57) ABSTRACT

A device for containing a graft material includes an outer member formed via an outer mesh sheet biased toward a coiled configuration in which the outer mesh sheet is coiled about a longitudinal axis thereof so that, when the outer member is positioned about separated portions of a target bone in an operative position, the outer member reverts to the coiled configuration and contracts about and engages the separated portions. The device also includes an inner mem- (Continued)

ber formed via an inner mesh sheet coiled about a longitudinal axis thereof. The inner member is movable between a first biased coiled configuration and a second coiled configuration. A diameter of the inner member in the first coiled configuration is larger than a diameter of the inner member in the second coiled configuration.

11 Claims, 5 Drawing Sheets

(56) References Cited

U.S. PATENT DOCUMENTS

| | | | |
|---|---|---|---|
| 8,092,513 B2 * | 1/2012 | Khosravi | A61F 2/92 606/191 |
| 9,925,046 B2 | 3/2018 | Larsen et al. | |
| 2001/0018616 A1 | 8/2001 | Schwab | |
| 2002/0123750 A1 * | 9/2002 | Eisermann | A61B 17/68 606/285 |
| 2004/0049270 A1 * | 3/2004 | Gewirtz | A61F 2/28 623/17.11 |
| 2005/0015154 A1 * | 1/2005 | Lindsey | A61B 17/68 623/23.46 |
| 2005/0192675 A1 | 9/2005 | Robinson | |
| 2005/0234557 A1 * | 10/2005 | Lambrecht | A61B 5/1076 623/17.16 |
| 2006/0282168 A1 * | 12/2006 | Sherman | A61B 17/1707 623/18.12 |
| 2007/0061015 A1 | 3/2007 | Jensen et al. | |
| 2007/0203584 A1 | 3/2007 | Bandyopadhyay et al. | |
| 2008/0269745 A1 | 10/2008 | Justin | |
| 2010/0310623 A1 | 12/2010 | Laurencin et al. | |
| 2011/0054408 A1 * | 3/2011 | Wei | A61B 17/68 604/175 |
| 2011/0307073 A1 | 12/2011 | Teoh et al. | |
| 2012/0029102 A1 * | 2/2012 | Rose | |
| 2012/0095463 A1 * | 4/2012 | Rains | A61B 17/68 606/63 |
| 2012/0296441 A1 * | 11/2012 | Mikhail | A61F 2/2803 623/23.63 |
| 2013/0018482 A1 | 1/2013 | Meridew et al. | |
| 2013/0261634 A1 * | 10/2013 | McKay | A61F 2/2846 606/93 |
| 2014/0364961 A1 | 12/2014 | Mikhail et al. | |

FOREIGN PATENT DOCUMENTS

| | | |
|---|---|---|
| EP | 1 800 627 | 6/2007 |
| KR | 2014/0005174 | 1/2014 |
| WO | 98/38918 | 9/1998 |
| WO | 02/064059 | 8/2002 |
| WO | 2009/025884 | 2/2009 |
| WO | 2010/011941 | 1/2010 |
| WO | 2010/044758 | 4/2010 |
| WO | 2010/093950 | 8/2010 |
| WO | 2011/094748 | 8/2011 |
| WO | 2012/068062 | 5/2012 |
| WO | 2013/006778 | 1/2013 |

* cited by examiner

BONE GRAFT CAGE

BACKGROUND

Large bone defects are often treated with implants and/or bone grafts to assist with healing. The bone grafts may be placed in the target area using any of a variety of methods. For example, a graft may simply be placed between two separated ends of an injured or otherwise damaged bone. However, without a container, the bone graft may fall away from a target site before it can be incorporated by the body into the healing bone. According to another method, PMMA spacers may be placed in the target area so that the fibrous tissue may be formed within the spacers. Subsequently, the PMMA spacers are removed and bone graft material is packed into the capsule formed by the body. Alternatively, some methods have included a mesh placed into the target area to contain the bone graft material at that location. These mesh containers generally include an outer wall with a diameter selected to match an outer surface of the bone to prevent the graft material from falling out of the bone.

SUMMARY OF THE INVENTION

The present invention is directed to a device for containing a graft material, comprising an outer member formed via an outer mesh sheet biased toward a coiled configuration in which the outer mesh sheet is coiled about a longitudinal axis thereof so that, when the outer member is positioned about separated portions of a target bone in an operative position, the outer member reverts to the coiled configuration and contracts about and engages the separated portions and an inner member formed via an inner mesh sheet coiled about a longitudinal axis thereof, the inner member movable between a first biased coiled configuration and a second coiled configuration, a diameter of the inner member in the first coiled configuration being larger than a diameter of the inner member in the second coiled configuration.

The present invention is also directed to a method for treating a bone with a bone graft material, comprising uncoiling an outer member from a biased coiled configuration to position the outer member about separated portions of a target bone, the outer member formed of an outer mesh sheet coiled about a longitudinal axis thereof in the coiled configuration and releasing the outer member so that the outer member reverts to the biased coiled configuration, the outer member contracting to engage the separated portions of the target bone.

BRIEF DESCRIPTION

DETAILED DESCRIPTION

The present invention may be further understood with reference to the following description and the appended drawings, wherein like elements are referred to with the same reference numerals. The present invention relates to the treatment of bone defects and, in particular, relates to treatments using bone grafts. Exemplary embodiments of the present invention describe a graft containment device configured to be positioned between separated longitudinal portions of a bone such that graft material may be packed therein so that healing may progress through the graft material to join the separated portions of bone. The graft containment device of the exemplary embodiment comprises an inner mesh member configured to be positioned within a medullary canal of a target area of a target bone and an outer mesh member configured to be positioned about the target area of the target bone. Graft material may be packed in a space between the outer and inner mesh members to promote bone growth in the target area. In another embodiment, for cases in which an intramedullary nail has been inserted into a medullary canal of a bone, the outer mesh material may be used alone by packing graft material between the outer mesh member and the intramedullary nail. The device of the present invention may be used to treat non-articular portions of long bone such as, for example, the femur, tibia and humerus.

As shown in FIGS. 1-7, a graft containment device 100 according to an exemplary embodiment of the present invention comprises an outer member 102 formed of a mesh sheet 104 pre-shaped in a coil configuration. The mesh sheet 104 is coiled so that the outer member 102 may be positioned in a target area 12 spanning a space separating longitudinal portions 14, 16 of a target bone 10. In particular, the outer member 102 is configured such that the outer member 102 coils about ends 18, 20 of the separated portions 14, 16 of the target bone 10, the shape of the outer member 102 substantially matching the profiles of the outer surface of each of the separated portions 14, 16 of the bone. For cases in which an intramedullary nail has been implanted into the target bone 10, graft material may be packed through openings 106 formed in the outer mesh component 102 against the intramedullary nail. Alternatively, the mesh sheet 104 of the outer coil member 102 may be opened (e.g., uncoiled) so that graft material may be packed therein, against the intramedullary nail. For cases in which an intramedullary nail has not been implanted in the target bone, the device 100 may further comprise an inner member 108 formed of a mesh sheet 110 pre-formed to coil about its longitudinal axis so that, when the inner member 108 is insertable into a medullary canal 22 of the target area 12, it assumes a coiled shape substantially matching a profile of the medullary canal 22 in which it is inserted. The inner member 108 according to this embodiment has a higher mesh density than the outer member 102—i.e., openings 112 defined by the mesh pattern of the inner member 108 are smaller than the openings 106 defined by the mesh pattern of the outer member 102—so that graft material packed through the openings 106 of the outer member 102 or by uncoiling the outer member 102 may be pressed against the inner member 108 without passing through the inner member 108 into the medullary canal.

Figure 1:
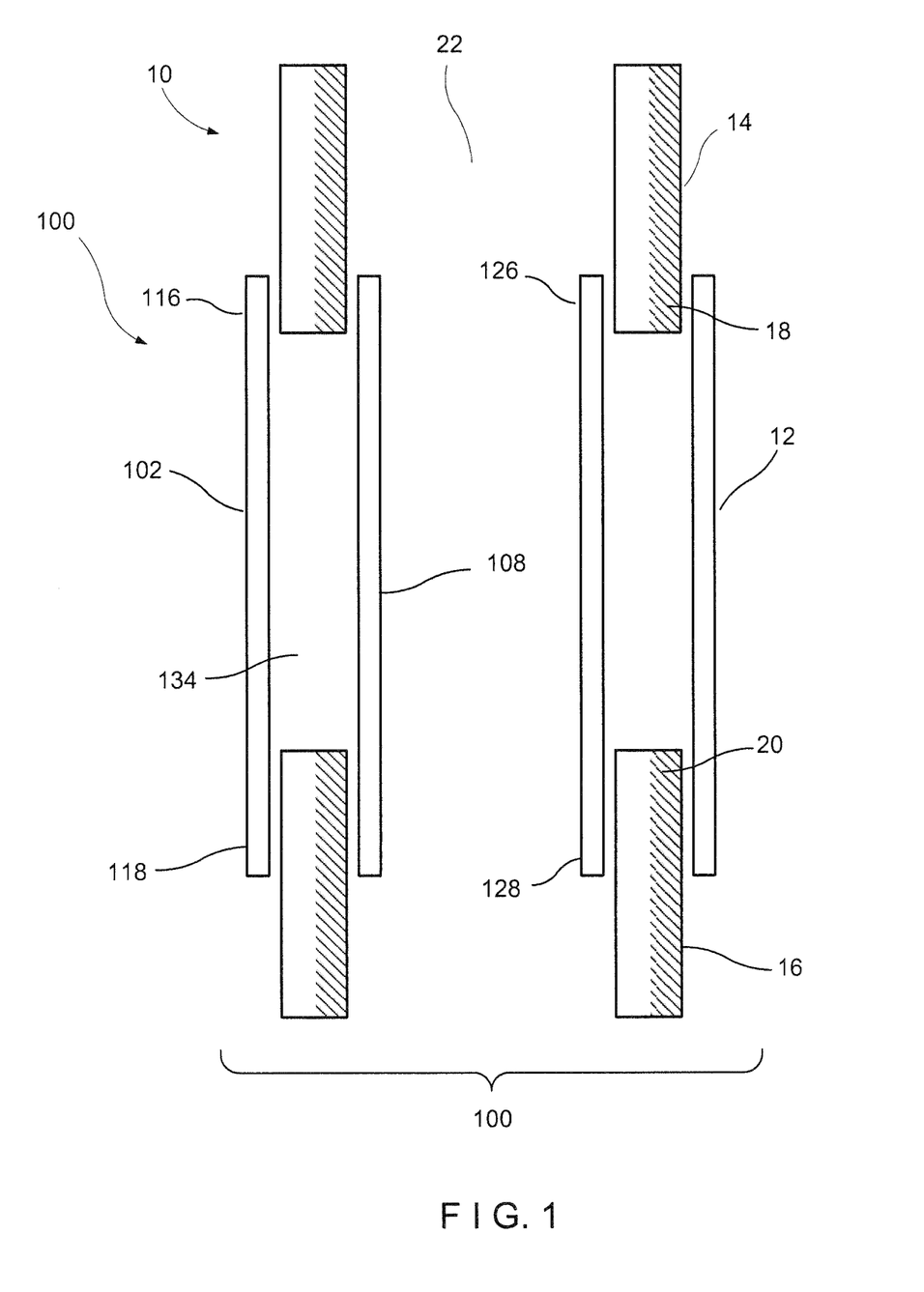
FIG. 1 shows a schematic plan view of a device according to an exemplary embodiment of the present invention.
Figure 2:
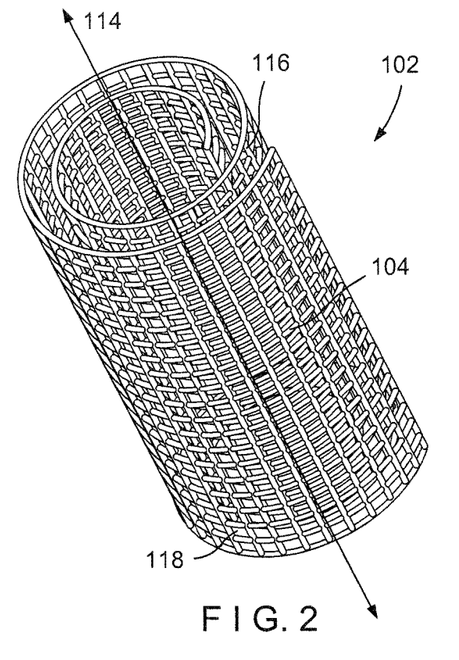
FIG. 2 shows a perspective view of an outer mesh member of the device of FIG. 1.
Figure 3:
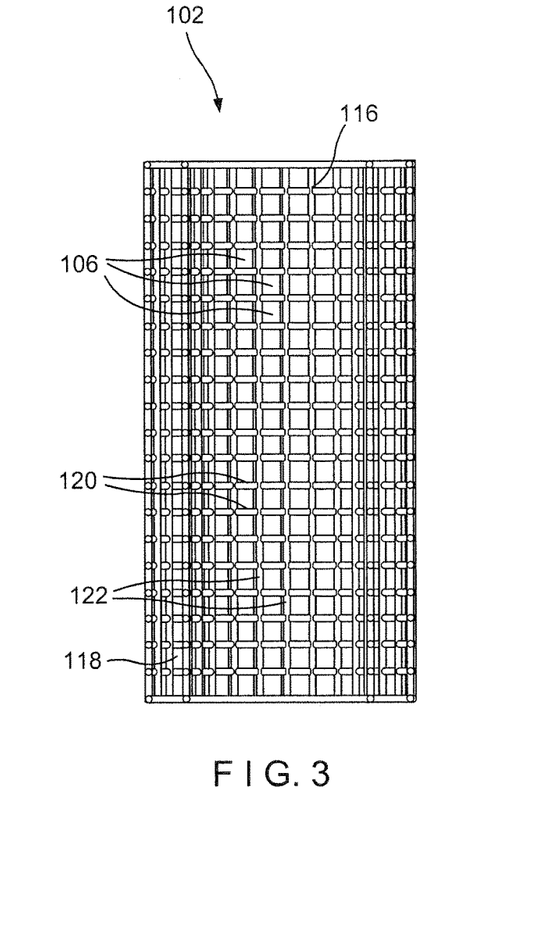
FIG. 3 shows a longitudinal cross-sectional view of the outer mesh member of the device of FIG. 1.
Figure 4:
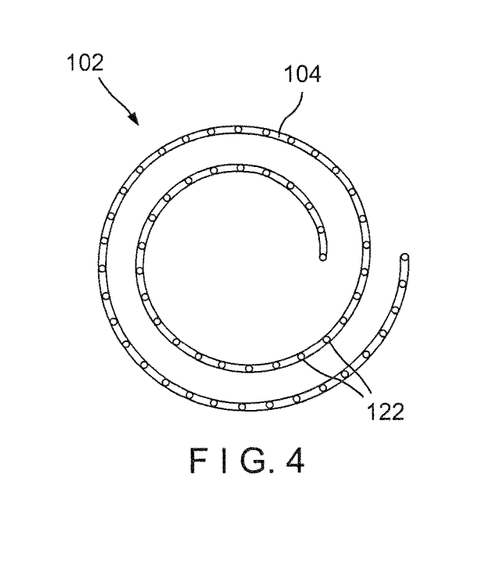
FIG. 4 shows a lateral cross-sectional view of the outer mesh member of the device of FIG. 1.

The outer member 102, as shown in FIGS. 2-4 and described above, is formed of the mesh sheet 104, which is pre-coiled about a longitudinal axis 114 so that a coil shape of the outer member 102 extends longitudinally from a proximal end 116 to a distal end 118. In other words, the mesh sheet 104 is biased toward the coil shape but may be uncoiled when positioning the outer member in the target area 12—e.g., so that the mesh sheet 104 may be wrapped around the ends 18, 20 of the separated portions 14, 16 of the bone 10. The coil shape of the outer member 102 is preferably selected so that, when the outer member 102 is positioned in the target area 12 wrapped about the separated portions 14, 16 of the target bone 10, the outer member 102 contracts about the ends 18, 20 of the separated portions 14, 16. The outer member 102 may be formed of a biodegradable polymer such as, for example, polycaprolactone (PCL), which permits the mesh sheet 104 to be uncoiled to position the outer member 102 in the target 12. In a desired position, the mesh sheet 104 should be placed in the target area 12 so that the proximal and distal ends 116, 118 overlap ends 18, 20 of the separated portions 14, 16. In this position, the longitudinal axis 114 of the outer coil member 102 will be substantially co-axial with or parallel to a longitudinal axis of the target bone. Upon placing the outer member 102 in a desired position in the target area 12, the outer member 102 is permitted to revert to its coiled configuration, collapsing about the target bone 10 to engage the ends 18, 20. The bioresorbable polymer material of the outer member 102 permits a user of the device 100 (e.g., surgeon) to cut the mesh sheet 104 to a desired size and shape to fit the target bone 10 of a specific patient.

The mesh sheet 104 of the outer member 102 is formed of a strut framework including, for example, a plurality of horizontal struts 120 and a plurality of longitudinal struts 122 intersecting one another to form a substantially grid-like pattern in which openings 106 are defined by the intersecting struts 120, 122. A diameter of each of the horizontal and longitudinal struts 120, 122 may range from between 1.0 mm and 2.0 mm. A spacing between adjacent horizontal struts 120 and adjacent longitudinal struts may range from between 1.0 mm and 10.0 mm. In one particular embodiment, the spacing between adjacent struts 120, 122 may be approximately 5.0 mm. Although the exemplary embodiment shows and describes the mesh sheet 104 as formed of horizontal and longitudinal struts 120, 122 intersecting to form a substantially grid-like mesh pattern, it will be understood by those of skill in the art that the mesh sheet 104 of the outer member 102 may be formed of any of variety of mesh patterns such as, for example, a diamond mesh pattern formed of diagonally extending intersecting struts, so long as the mesh pattern is formed via a strut framework.

Figure 5:
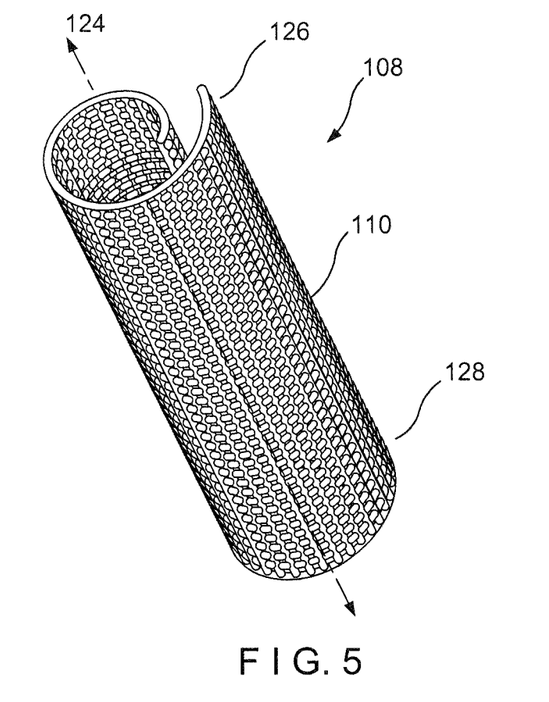
FIG. 5 shows a perspective view of an inner mesh member of the device of FIG. 1.
Figure 6:
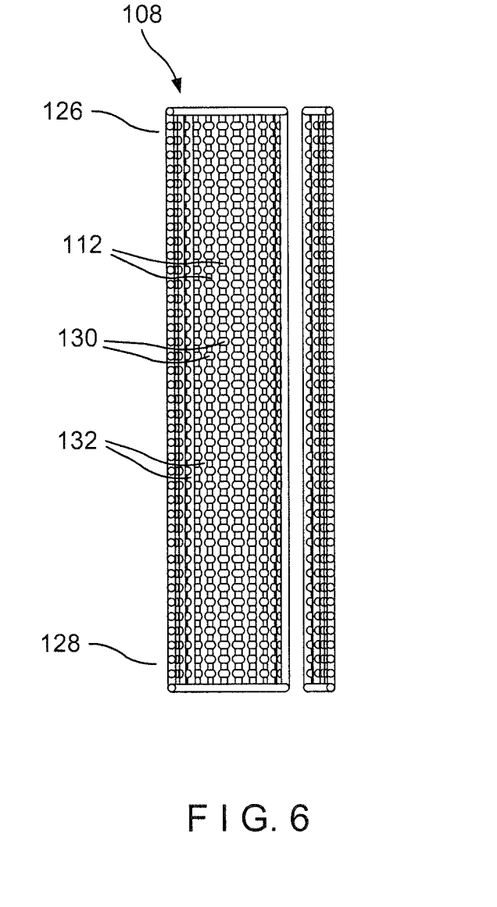
FIG. 6 shows a longitudinal cross-sectional view of the inner mesh member of the device of FIG. 1.
Figure 7:
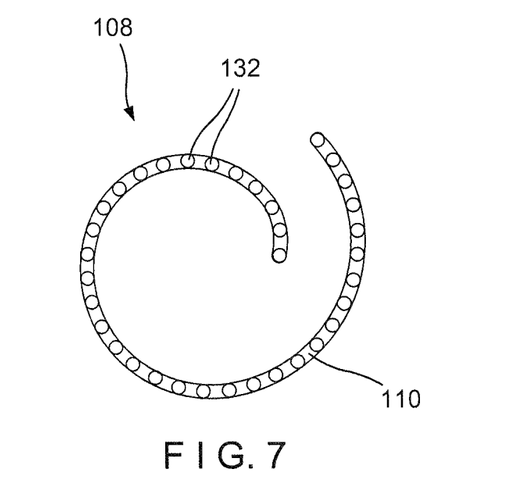
FIG. 7 shows a lateral cross-sectional view of the inner mesh member of the device of FIG. 1.

The inner member 108, as shown in FIGS. 5-7 and as described above, includes the mesh sheet 110, which is pre-coiled about a longitudinal axis 124 so that a coil-shape of the inner member 108 extends longitudinally from a proximal end 126 to a distal end 128. The coil shape of the inner member 108 is such that, when the inner member 108 is positioned within the medullary canal 22 at the target area 12, the inner member 108 expands to abut the walls of the medullary canal in the separated portions of bone 14, 16. In particular, the inner member 108 is movable between a biased first coil configuration and a second coil configuration, a diameter of the inner member 108 being larger in the first configuration than in the second configuration. Similarly to the outer member 102, the inner member 108 may be formed of a bioresorbable polymer (e.g., PCL) having sufficient flexibility so that coil shape of the inner member 108 may be contracted or tightened from the biased first configuration to the second configuration for insertion into the medullary canal 22. In other words, a diameter of the coil shape of the inner member 108 may be reduced to facilitate insertion of the inner member 108 into the medullary canal 22. When in the desired position in the medullary canal 22, the proximal and distal ends 128 extend into the ends 18, 20, respectively, of the separated portions 14, 16 of the target bone 10. In this position, the inner member 108 is permitted to revert to the biased first configuration, expanding to abut the wall of the medullary canal 22. Similarly to the outer member 102, the mesh sheet 110 of the inner member 108 may be cut down to a desired size and shape to suit the needs of a particular patient.

The mesh sheet 110 of the inner member 108 is also formed via a strut framework which in this embodiment includes a plurality of horizontal struts 130 and a plurality of longitudinal struts 132 intersecting one another in a substantially grid-like pattern to define openings 112. A diameter of each of the horizontal and longitudinal struts may range, for example, between 1.0 mm and 2.0 mm. A spacing between adjacent one of the horizontal and longitudinal struts 130, 132 may range, for example, between 1.0 mm and 5.0 mm. In one particular embodiment, the spacing between adjacent struts is approximately 2.5 mm. The spacing between adjacent struts 130, 132 of the inner member 108, however, should be smaller than the spacing between adjacent struts 120, 122 of the outer member 102. The spacing between adjacent struts 130, 132 of the inner member 108 may be particularly selected so that graft material packed thereagainst is prevented from passing into the medullary canal through the openings 112 defined by the intersecting horizontal and longitudinal struts 130, 132. Although the exemplary embodiment shows and describes the mesh sheet 110 of the inner member 108 as having a substantially grid-like pattern, the mesh sheet 110 may have any of a variety of mesh patterns so long as the mesh pattern is defined via a plurality of intersecting struts in a strut framework. For example, the mesh sheet 110 may also be formed via diagonally extending intersecting struts to form a diamond mesh pattern.

Upon positioning the outer and inner members 102, 108 as described above, graft material may be packed in a space 134 therebetween via the openings 106 of the outer member 102. Alternatively, the outer member 102 may be opened (e.g., uncoiled) so that the graft material may be packed in the coil of the outer member 102 and, against the inner member 108. In cases in which the inner member 108 is not necessary because the device 100 is being used with an intramedullary nail, the graft material may be packed in a space between the intramedullary nail and the outer member 102. The outer and inner members 102, 108 may be built and printed using, for example, CAD software, by defining a size of the outer and inner members 102, 108 and a spacing between adjacent struts so that manufacturing the device 100 is simple and cost-effective. Bioresorbable polymers, such as PCL, are able to be printed while also being cuttable using cutting tools so that the device 100 may be tailored to specific patient needs and dimensions.

According to an exemplary method using the device 100, the inner member 108 may be contracted and positioned within the medullary canal 22 at the target area 12 of the target bone 10 so that proximal and distal ends 126, 128 of the inner member 108 are received within the ends 18, 20 of the separated portions 14, 16 of the target bone 10. As described above, prior to insertion in the medullary canal, the inner member 108 may be cut down to adjust a length and/or width (i.e., diameter) thereof. Upon positioning the inner member 108 in the desired position within the medullary canal 22, the inner member 108 is permitted to revert to its pre-formed coiled configuration, expanding to fill the medullary canal 22. In other words, the a diameter of the inner member 108 is permitted to increase so that the inner member 108 comes into contact with a surface of the medullary canal 22 within the ends 18, 20 of the separated portions 14, 16 of the target bone 10 so that the inner member 108 substantially adapts to match a profile of the medullary canal 18. In one embodiment, a width of the inner member 108 may be cut to substantially correspond to a size of the medullary canal so that, upon expansion therein, longitudinal edges of the inner member 108 may be sutured or otherwise affixed to maintain the inner member 108 in a closed configuration. In another embodiment, upon expansion in the medullary canal, longitudinal edges of the inner member 108 may overlap such that the suturing and/or affixing of edges is not required.

Similarly to the inner member 108, the outer member 102 may be cut to suit a patient's specific needs and dimensions. Once the outer member 102 has been cut to a desired size, the outer member 102 may be uncoiled and positioned in the target area 12 so that the proximal and distal ends 116, 118 overlap the ends 18, 20 of the separated portions 14, 16. The outer member 102 may then be released to permit the outer member 102 to revert to its coiled configuration, contracting about the ends 18, 20 to substantially match a profile of an outer surface of the target bone 10. Longitudinal edges of the outer member 102 may be sutured or otherwise affixed together to maintain the coiled shape of the outer member 102. Upon positioning of both the inner and outer member 108, 102, graft material may be packed through the openings 106 of the outer member 102 against inner member 108 until a space between the inner and outer members 108, 102 is filled with the graft material. As described above, the openings 112 of the inner member 108 are sized to prevent the graft material from being passed therethrough into the medullary canal 22.

The above exemplary method describes the use of the inner member 108, for cases in which an intramedullary nail has not already been implanted in the medullary canal of the target bone 10. For example, rather than fixing the separated portions 14, 16 of the target bone 10 relative to one another via an intramedullary nail, the separated portions 14, 16 may have been fixed via a bone plate or other bone fixation implant. For cases in which an intramedullary nail is also being used, the inner member 108 is not necessary. Instead, the user may simply position and mount the outer member 102 in the target area 12 over the target bone 10, as described above. The graft material is then packed through the openings 106 thereof against the intramedullary nail until a space between the intramedullary nail and the outer member 102 is filled with the graft material.

Figure 8:
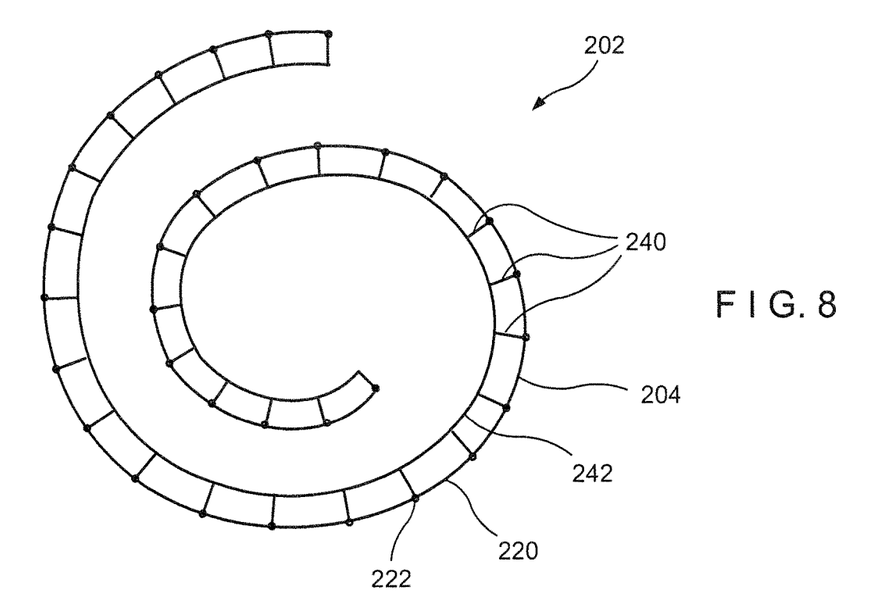
FIG. 8 shows a lateral cross-sectional view of an outer mesh member according to another exemplary embodiment of the present invention.
Figure 9:
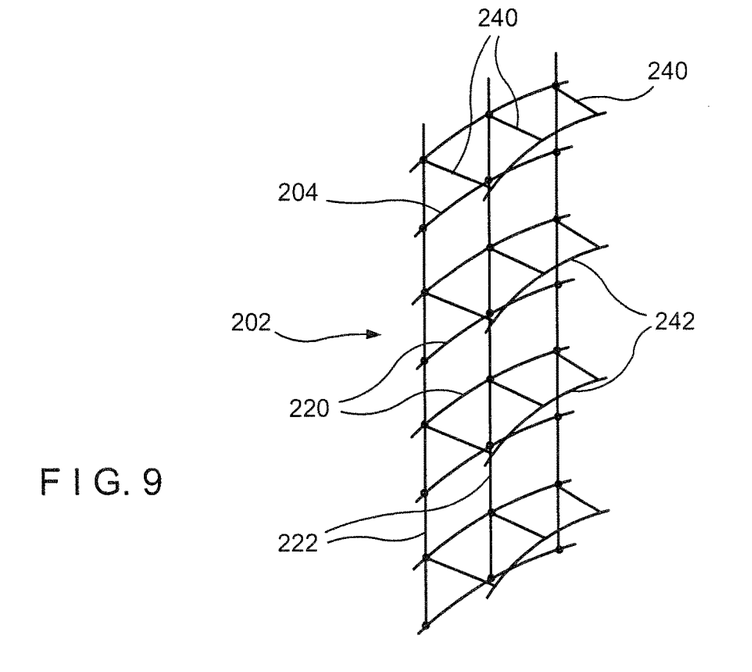
FIG. 9 shows a partial perspective view of the outer mesh member of FIG. 8.

As shown in FIGS. 8-11, a graft containment device according to another exemplary embodiment of the present invention is substantially similar to the device 100 except as pointed out below. The device according to this embodiment comprises an outer member 202 formed of a mesh sheet 204 pre-shaped in a coil configuration so that outer member 102 coils about separated portions of a bone to substantially match an outer surface of portions of the bone and an inner member 208 formed of a mesh sheet 210 pre-formed in a coiled configuration so that, when inserted into a medullary canal of the bone, the inner member 208 substantially matches a profile of the medullary canal. The outer member 202 may be substantially similar to the outer member 102. As shown in FIGS. 8 and 9, the outer member 202 may further include, however, a plurality of ribs 240 extending radially inward from the mesh sheet 204. The ribs 240 may extend substantially perpendicularly from an interior surface of the mesh sheet 204. In one example, each of the ribs 240 may extend from a point at which horizontal and longitudinal struts 220, 222 forming the mesh sheet 204 intersect and may have a length of approximately 5.0 mm. Radially innermost ends of horizontally adjacent ones of the ribs 240 may be connected via coiled horizontal struts 242.

Figure 10:
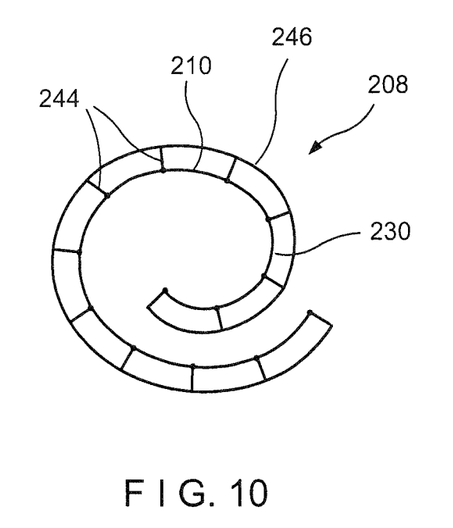
FIG. 10 shows a lateral cross-sectional view of an inner mesh member according to another exemplary embodiment of the present invention.
Figure 11:
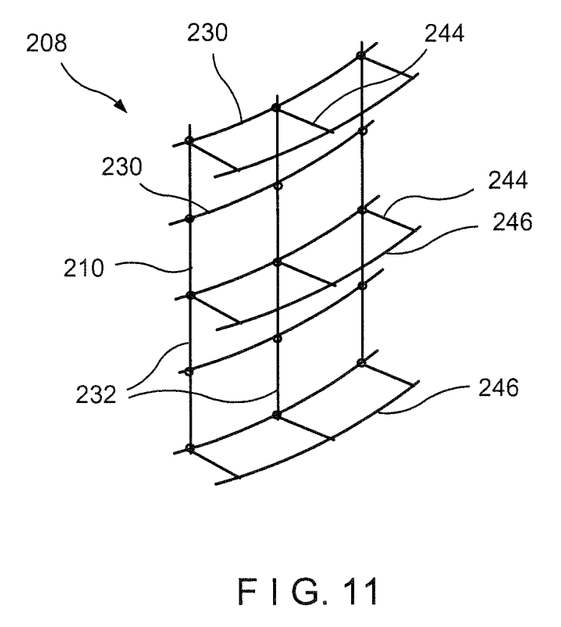
FIG. 11 shows a partial perspective view of the inner mesh member of FIG. 10.

As shown in FIGS. 10-11, the inner member 208 is substantially similar to the inner member 108 except as pointed out below. The inner member 208 further includes a plurality of ribs 244 extending radially outward from the mesh sheet 210. The ribs 244 may extend substantially perpendicularly from an exterior surface of the mesh sheet 210. In one example, each of the ribs 244 may extend from a point at which horizontal and longitudinal struts 230, 232 forming the mesh sheet 210 intersect and has a length of approximately 5.0 mm. Radially outermost ends of horizontally adjacent ones of the ribs 244 are connected via coiled horizontal struts 246.

The outer and inner members 202, 208 of the device 200 may be used in a manner substantially similarly to the device 100. The ribs 240, 244, however, act as axial stabilizers preventing axial migration of graft material packed between the outer and inner members 202, 208 or between the outer member 202 and an intramedullary nail for cases in which an intramedullary nail within the medullary canal renders the inner member 208 unnecessary. Ribs 240 extend along portions of the outer member 202 which overlap portions of the bone. These portions may be trimmed or cut off during sizing of the outer member 202 to avoid interference with the portions of bone over which they extend, as described above in regard to the device 100. Similarly, ribs 244 extending along portions of the inner member 208 which overlap a surface of the medullary canal may be trimmed or cut away to avoid interference with the medullary canal.

Although the exemplary embodiment describes both the outer member 202 and the inner member 208 as including ribs 240, 244, respectively, it will be understood by those of skill in the art that, in some cases, it may be desired for only one of the outer and inner members 202, 208 to include ribs.

It will be understood by those of skill in the art that various modification and variations may be made in the structure and methodology of the present invention, without departing from the spirit or the scope of the invention. Thus, it is intended that the present invention cover the modifications and variations of this invention provided that they come within the scope of the appended claims and their equivalents.

What is claimed is:
1. A device for containing a graft material, comprising:
an outer member formed via an outer mesh sheet biased toward a coiled configuration in which the outer mesh sheet is coiled about a longitudinal axis thereof so that, when the outer member is positioned about separated portions of a target bone in an operative position, the outer member reverts to the coiled configuration and contracts about and engages the separated portions; and an inner member formed via an inner mesh sheet coiled about a longitudinal axis thereof, the inner member movable between a first biased coiled configuration and a second coiled configuration, a diameter of the inner member in the first coiled configuration being larger than a diameter of the inner member in the second coiled configuration so that, when the inner member is positioned within a medullary canal of the target bone in an operative position, the inner member reverts to the first biased coiled configuration and expands to engage walls of the medullary canal, wherein at least a portion of the inner member is configured to be received within the outer member, wherein the inner member has a higher mesh density than the outer member.

2. The device of claim 1, wherein one of the outer member and the inner member is formed of a plurality of longitudinal struts and a plurality of horizontal struts intersecting one another.

3. The device of claim 2, wherein each of the plurality of longitudinal and horizontal struts have a diameter ranging from between 1.0 mm and 2.0 mm.

4. The device of claim 2, wherein a spacing between adjacent ones of the horizontal struts and adjacent ones of the longitudinal struts range from between 1.0 mm and 10.0 mm.

5. The device of claim 1, wherein one of the outer member and the inner member are formed of a bioresorbable polymer material.

6. The device of claim 5, wherein the bioresorbable polymer material is polycaprolactone.

7. The device of claim 1, further comprising a first plurality of ribs extending radially inward from an interior surface of the outer member.

8. The device of claim 7, further comprising a plurality of first coiled horizontal struts connecting radially innermost ends of adjacent ones of the first plurality of ribs.

9. The device of claim 1, further comprising a second plurality of ribs extending radially outward from an exterior surface of the inner member.

10. The device of claim 9, further comprising a plurality of second coiled horizontal struts connecting radially outermost ends of adjacent ones of the second plurality of ribs.

11. The device of claim 1, wherein the outer member and the inner member are formed of a plurality of diagonally extending struts intersecting one another to form a diamond mesh pattern.

* * * * *